US012714975B2

(12) United States Patent
Kastantin et al.

(10) Patent No.: US 12,714,975 B2
(45) Date of Patent: Aug. 25, 2026

(54) METHODS AND SYSTEMS FOR SPRAY DRYING TEMPERATURE SENSITIVE PRODUCTS

(71) Applicant: Serán BioScience, LLC, Bend, OR (US)

(72) Inventors: Mark Kastantin, Bend, OR (US); Dan Smithey, Bend, OR (US); Erica Schlesinger, Sisters, OR (US); Tony Vickery, Bend, OR (US); Ryan Mowry, Bend, OR (US); Tanner Corrado, Bend, OR (US)

(73) Assignee: SERÁN BIOSCIENCE, LLC, Bend, OR (US)

( * ) Notice: Subject to any disclaimer, the term of this patent is extended or adjusted under 35 U.S.C. 154(b) by 56 days.

(21) Appl. No.: 18/527,157

(22) Filed: Dec. 1, 2023

(65) Prior Publication Data

US 2024/0181412 A1 Jun. 6, 2024

Related U.S. Application Data

(60) Provisional application No. 63/385,928, filed on Dec. 2, 2022.

(51) Int. Cl.
*B01J 2/00* (2006.01)
*A61K 9/16* (2006.01)
*B01J 2/06* (2006.01)

(52) U.S. Cl.
CPC ............... *B01J 2/06* (2013.01); *A61K 9/1623* (2013.01); *A61K 9/1682* (2013.01)

(58) Field of Classification Search
CPC ........................................................ B01J 2/06
See application file for complete search history.

(56) References Cited

U.S. PATENT DOCUMENTS 5,667,806 A * 9/1997 Kantor ..................... B01J 13/02 424/490
8,966,783 B2 3/2015 Kitamura et al.
2005/0031692 A1* 2/2005 Beyerinck ............ A61K 31/401 424/486
2015/0257402 A1* 9/2015 Sipahioglu ............... A23C 1/16 426/588

OTHER PUBLICATIONS

Sadeghzade Namavar, et al, M.A., 2018. A multi-objective optimization of artichoke (*Cynara scolymus* L.) leaves aqueous extraction dehydration through a novel spray drying approach using response surface methodology. Iranian Journal of Chemistry and Chemica (Year: 2018).*
https://volupe.com/simcenter-star-ccm/6831-2/ (Year: 2022).*

* cited by examiner

*Primary Examiner* — Nicholas Krasnow
(74) *Attorney, Agent, or Firm* — McCoy Russell LLP

(57) ABSTRACT

Systems and methods are provided for vacuum spray drying. In one example, a method for spray drying includes estimating an outlet temperature to achieve a minimum drying rate at atmospheric pressure based on a selected liquid feed and a selected liquid to gas ratio, calculating a predicted dryer pressure at which the minimum drying rate can be reached at a reduced outlet temperature, and spray drying the selected liquid feed at the selected liquid to gas ratio, the predicted dryer pressure and the reduced outlet temperature. The reduced outlet temperature is less than a maximum temperature and the predicted dryer pressure includes an approximation for droplet solidification.

14 Claims, 9 Drawing Sheets

526
Exhaust
524
525
518
522
Liquid Exhaust
520
516
515
512
514
508
510
507
602
Liquid Feed
Heated Gas
506
604
502
509
504
600

METHODS AND SYSTEMS FOR SPRAY DRYING TEMPERATURE SENSITIVE PRODUCTS

CROSS REFERENCE TO RELATED APPLICATIONS

The present application claims priority to U.S. Provisional Application No. 63/385,928 entitled "METHODS AND SYSTEMS FOR SPRAY DRYING TEMPERATURE SENSITIVE PRODUCTS" filed Dec. 2, 2022. The entire contents of the above identified application is hereby incorporated by reference for all purposes.

FIELD

The present description relates generally to spray drying temperature sensitive products under vacuum conditions.

BACKGROUND/SUMMARY

Spray drying is a technique commonly used in the production of pharmaceuticals. Spray drying includes introducing fine droplets of a suspension or solution to a drying chamber and interacting the fine droplets with a stream of hot gas. The energy from the hot gas vaporizes a liquid phase of the suspension or solution, leaving behind solid particles. Often, spray drying is done at atmospheric pressures, but under some circumstances vacuum spray drying (VSD) is demanded, wherein a pressure inside the drying chamber is maintained below atmospheric pressure. For example, the product being dried may be heat sensitive. Reducing pressure inside, the drying chamber increases the mass flux away from a vapor-liquid interface at a fixed temperature. Relative to an atmospheric pressure drying process, the drying temperature of a VSD process may be lowered while achieving the same drying rate. As another example, the liquid phase may include a high boiling solvent such a dimethyl sulfoxide (DMSO) which may demand reduced pressures in order to efficiently remove the liquid phase. However, under vacuum conditions, efficiency of heat transfer from the heated gas to the droplets may be reduced, thereby reducing a drying rate and a maximum throughput when using VSD.

Other attempts to address low throughput include modifications to a VSD system to enhance heat transfer. One example of this approach is shown in U.S. Pat. No. 8,966,783. Therein, high throughputs are achieved by supplying a superheated fluid to immediately contact the suspension/solution droplets upon introduction to the vacuum environment.

However, the inventors herein have recognized potential issues with such systems. As one example, the low boiling points achieved by such systems may still be too hot for some temperature sensitive pharmaceutical products. If decreasing the drying chamber pressure is used alone as a mechanism used to reduce temperature experienced by the product, a size of a vacuum pump demanded for a throughput used for manufacturing may be impractically large.

In one example, the issues described above may be at least partially addressed by a method of spray drying including, estimating an outlet temperature to achieve a minimum drying rate at atmospheric pressure based on a selected liquid feed and liquid to gas ratio; calculating a predicted dryer pressure at which the minimum drying rate can be reached at a reduced outlet temperature wherein the reduced outlet temperature is less than a maximum temperature, and wherein the predicted dryer pressure includes an approximation for droplet solidification; and spray drying the selected liquid feed at the selected liquid to gas ratio, the predicted dryer pressure, and the reduced outlet temperature. In this way, products may be dried at temperatures that do not degrade the product. Additionally, process conditions under which drying rates may be adequate when using conventionally sized spray drying equipment may be identified. Further, modifications to a conventional spray drying system including extending the spray dryer may be used when drying rates are identified as inadequate. Additionally, in an example where vacuum conditions are demanded within the spray drying system, a modified cyclone design may be used to decrease a chamber pressure achieved for a given vacuum pump power.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 2:
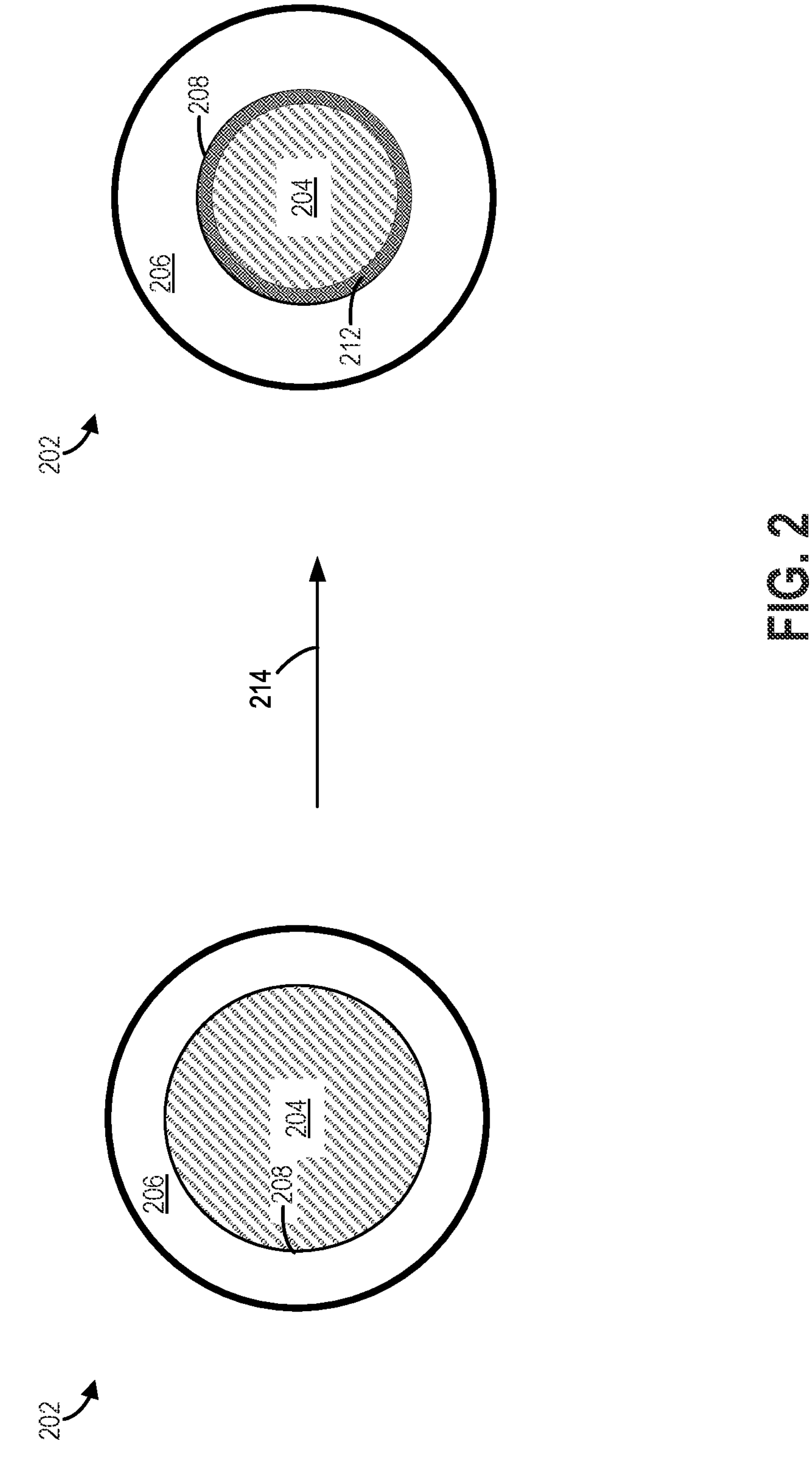
FIG. 2 shows an illustration of a droplet as time elapses during a spray drying process.
Figure 3:
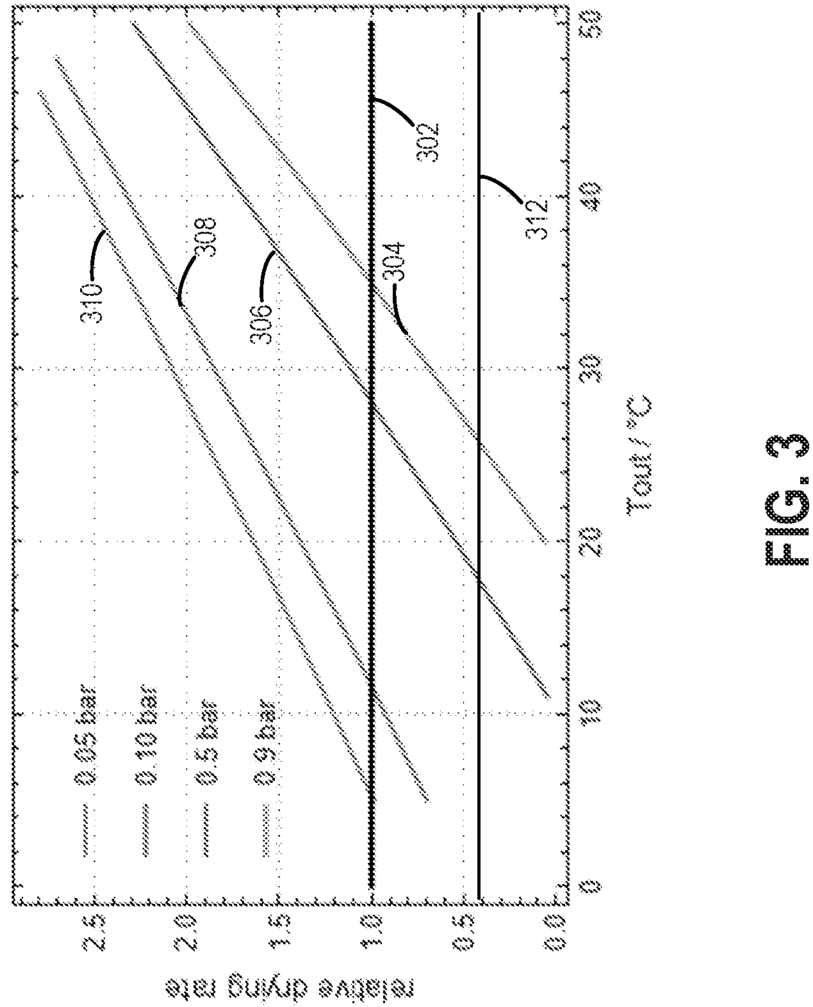
FIG. 3 shows a graph of relative drying rate as a function of drying chamber outlet temperatures calculated for a range of drying chamber pressures.
Figure 3:

The following description relates to systems and methods for spray drying temperature sensitive products. In one example, a vacuum spray drying (VSD) system such as the system shown schematically in FIG. 1 may be used to spray dry temperature sensitive products. Decreasing a pressure in the drying chamber of the VSD may result in acceptable drying rates under reduced temperatures. A desired chamber pressure and spray dryer configuration capable of drying at below a selected maximum temperature may be chosen based on a model of liquid evaporation from a droplet as illustrated in FIG. 2. Using a set of reference conditions (e.g., chamber pressure, outlet temperature, and liquid to gas ratio) a graph of relative drying rate as a function of outlet temperature for a range of chamber pressures may be drawn, as shown in FIG. 3. As one example, a desired minimum relative drying rate (e.g., 1), a chamber pressure corresponding to a desired outlet temperature may be calculated following a method shown as a flow chart in FIG. 4A and FIG.

Figure 5:
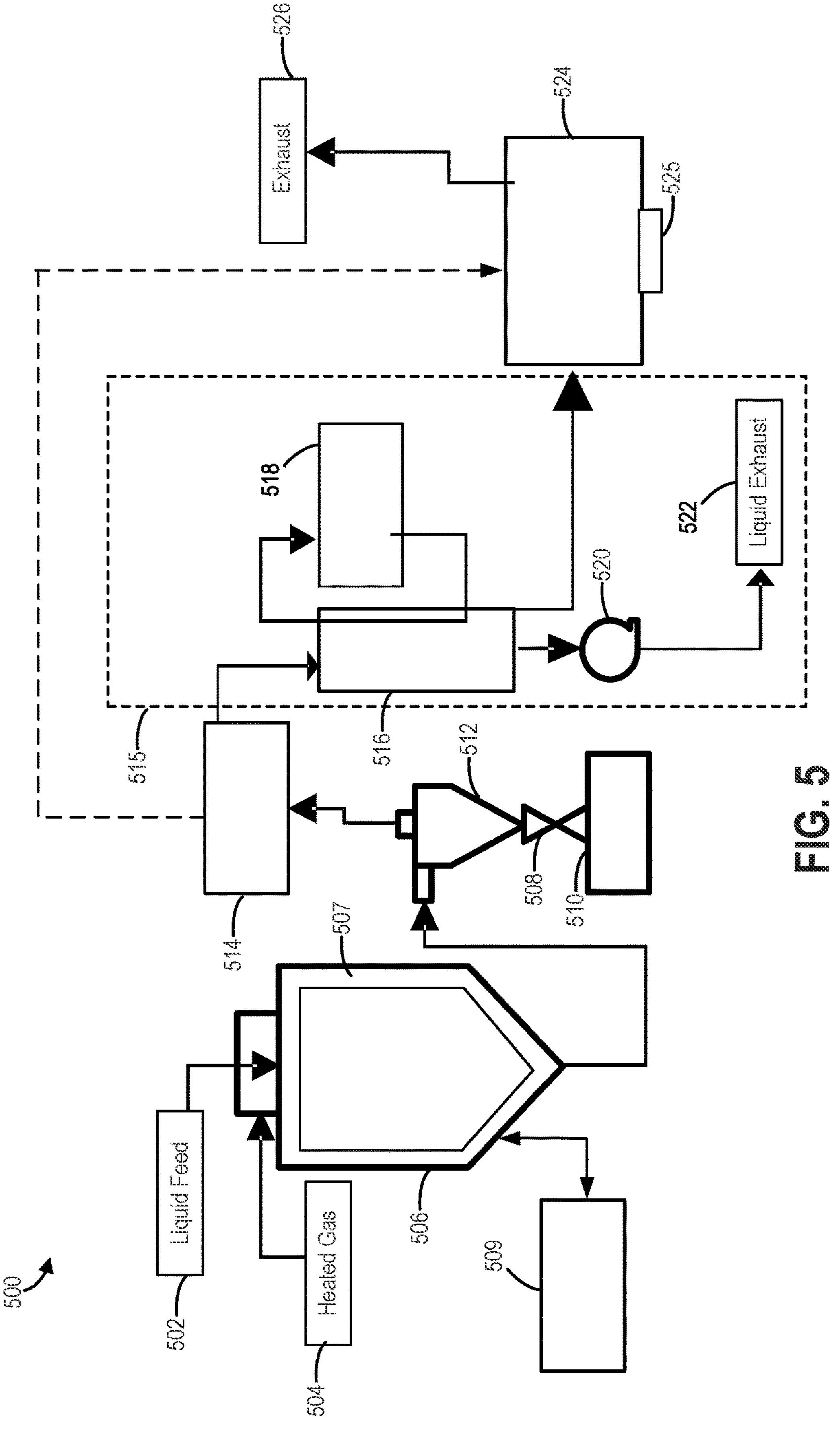
FIG. 5 shows an example of a co-current vacuum spray drying system.
Figure 6:
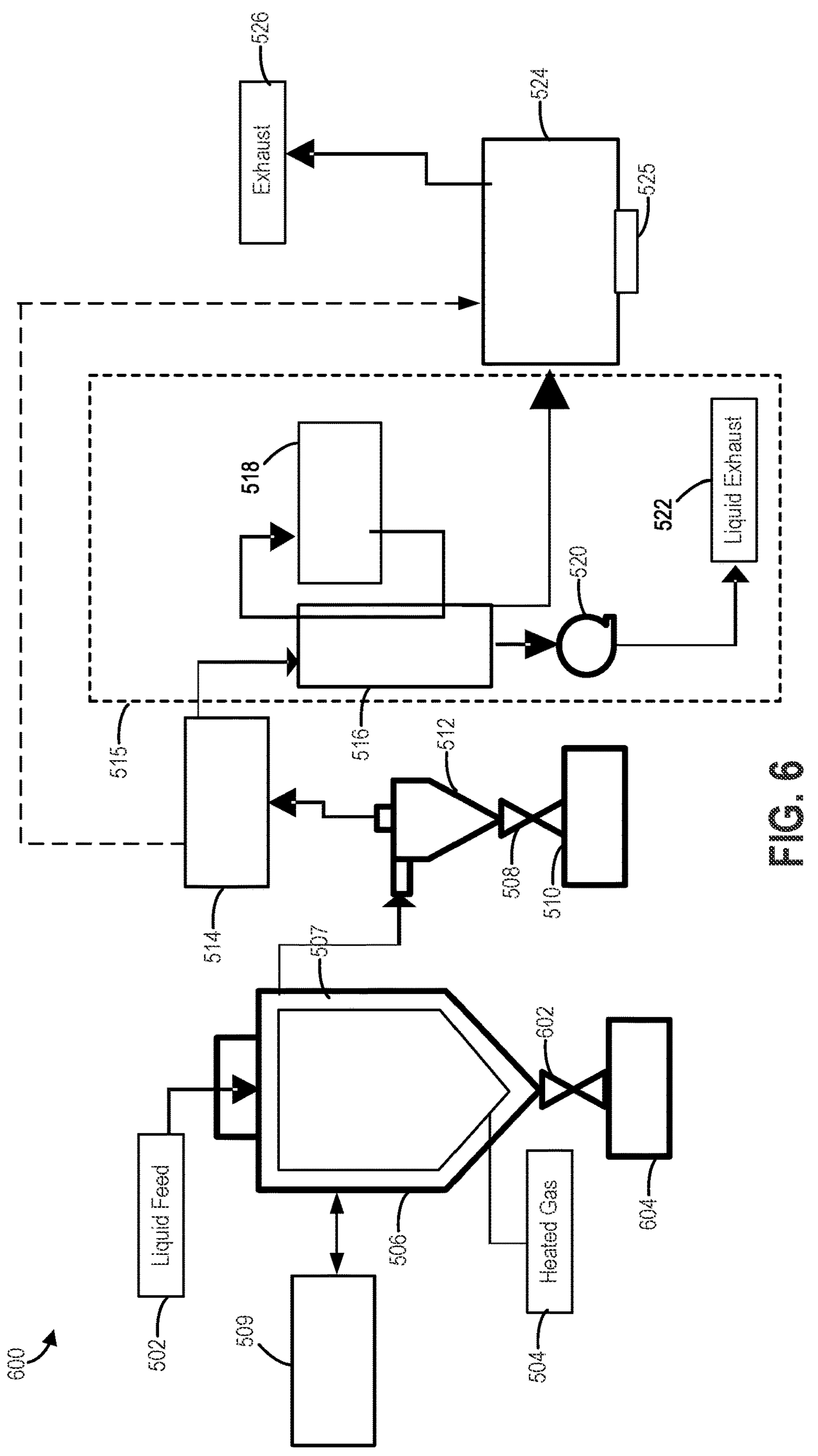
FIG. 6 shows an example of a counter-current vacuum spray drying system.

4B. In some examples, the desired minimum rate may depend on a configuration of the VSD, including a height of the drying chamber, a configuration of a liquid and a gas feeds, and a size of the cyclone. An example of VSD with the liquid feed and the gas feed in a co-current configuration is shown in FIG. 5 and an example of a VSD with the liquid feed and the gas feed in the counter-current configuration is shown in FIG. 6. The size of the cyclone may influence minimum pressure of the VSD system due to an increased pressure drop across the cyclone with decreasing cyclone dimensions. Increasing a cyclone size may decrease a minimum pressure of a VSD and decreasing a cyclone size may increase a minimum pressure of VSD. As an example, pressure drop as function of gas flow is shown for a cyclone with a two-inch diameter and a cyclone with a three-inch diameter in FIG. 7 and FIG. 8 respectively.

Figure 1:
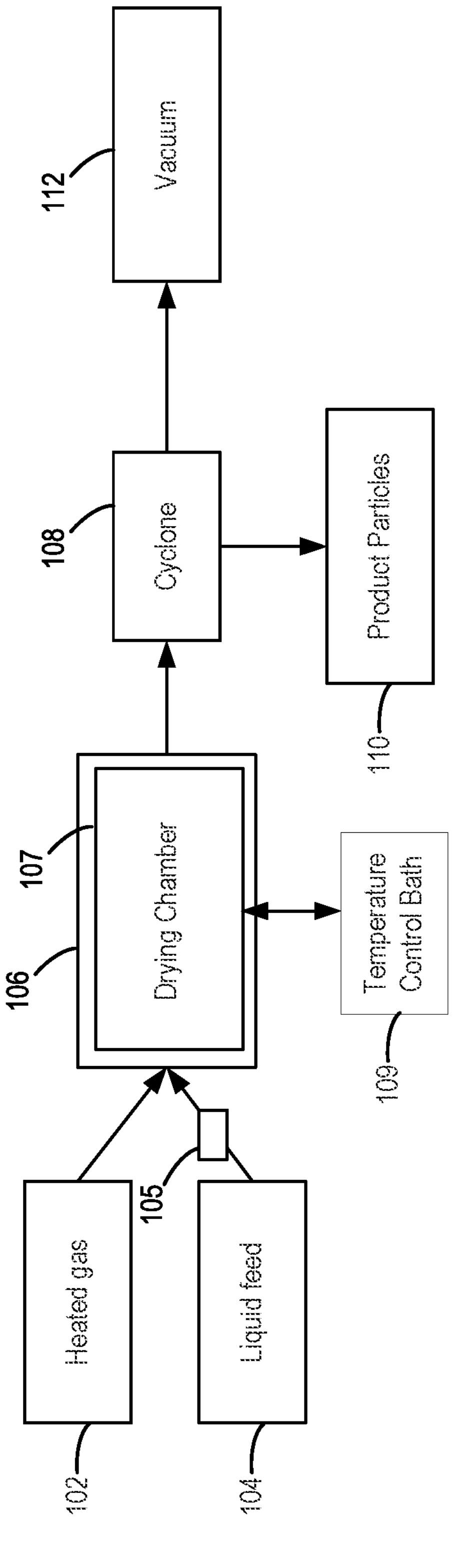
FIG. 1 shows a block diagram of a workflow for spray drying compounds at reduced pressures.
Figure 1:

Turning now to FIG. 1, a schematic diagram of a vacuum spray drying (VSD) system 100 is shown. VSD system 100 may include a drying chamber 106. Drying chamber 106 may be configured to receive a heated gas 102 and a liquid feed 104. In some examples, drying chamber 106 may be a jacketed drying chamber, including jacket layer 107 fluidly coupled to a temperature control bath 109. By setting a temperature of temperature control bath 109, a user may actively control a temperature of drying chamber 106. Under vacuum conditions, heated gas 102 may be flowed at a lower mass flow rate when compared to conventional (e.g., atmospheric pressure) spray drying. The lower mass flow rate may result in a larger influence of environmental heat exchange on an operating temperature (e.g., outlet temperature) of drying chamber 106. Jacket layer 107 and temperature control bath 109 may insulate drying chamber from heat exchange with the environment and provide increased accuracy in controlling the operating temperature of drying chamber 106. Additionally, jacket layer 107 and temperature control bath 109 may enable spray drying at temperatures below an ambient room temperature.

Liquid feed 104 may be a suspension or solution including a liquid phase and a product either suspended or dissolved in the liquid phase. VSD system 100 may be configured to dry products which are sensitive to high temperatures. As one example, the product may be an active pharmaceutical ingredient (API) in a pharmaceutical formulation. The pharmaceutical formulation may include the API and other excipients. As one example, the API may be a pharmaceutically active protein (e.g., antibodies, enzymes, bacteriophages, cytokines, hormones, etc.). In some examples, the product may be a model compound that is used as a stand in for an API. The model compound may be useful for testing drying methods before drying more expensive APIs. Model compounds may include bovine serum albumin (BSA), model antibodies, and lysozymes, among others. A certain secondary, tertiary and quaternary structure of proteins may be demanded for the protein to be pharmaceutically active. High temperatures may damage the structure of proteins, thereby rendering them inactive. As another example, the API may include nucleic acids such as DNA or RNA. Types of RNA may include but are not limited to messenger RNA (mRNA), transfer RNA (tRNA), and/or short interfering (siRNA). High temperatures may increase a rate of hydrolysis which may degrade nucleic acids. As a further example, the API may be a self-assembled nanoparticle encapsulating a pharmaceutical compound. The self-assembled nanoparticle may be formed of biologically compatible molecules appropriate for pharmaceutical formulations. For example, the self-assembled nanoparticle may be formed of lipids, block copolymers, amphiphilic polymer (e.g., hypromellose acetate succinate) or the like. In some examples, the self-assembled nanoparticle may not be an API, but may be a carrier for the API. For example, the self-assembled nanoparticle may for a hollow shell which encapsulates the API. For example, a lipid nanoparticle encapsulating an RNA fragment may be spray dried. A structure of self-assembled nanoparticles may be altered by high heat, thereby exposing and degrading the encapsulated pharmaceutical compound upon drying. As an additional example, the product may be an amorphous solid dispersion of a small molecule API. As one example, the small molecule may be between 100 Da and 2,000 Da. Exposure to high temperatures may induce crystallization of the API, thereby degrading an effectiveness of the API.

The liquid phase may be water or a high volatility organic solvent having a boiling point of 100° C. or lower at standard pressure (e.g., acetone, methanol, ethanol, isopropyl alcohol, ethyl acetate, etc., or some combinations thereof). As one example, the liquid phase may be 100% water. As an alternate example, the liquid phase may be between 50% and 100% water by weight and less than or equal to 50% organic solvent by weight. As a further example, the liquid phase may include between 5%-100% low-volatility organic solvent. The low volatility organic solvent may be an organic solvent having a boiling point above 150° C. at standard pressure (e.g., 1 atm) such as dimethyl sulfoxide (DMSO), dimethylformamide (DMF), N-methyl-2-pyrrolidone (NMP), or N,N-dimethylacetamide (DMAC). A remainder of the liquid phase may be comprised of a miscible co-solvent which may be water or a high volatility organic solvent.

Heated gas 102 may be air or nitrogen, for example. Nitrogen may be used as heated gas 102 when the product is prone to oxidation or if the liquid phase is flammable. Heated gas 102 and liquid feed 104 may be introduced into drying chamber 106. Liquid feed 104 may enter drying chamber 106 through an atomizer 105. Atomizer 105 may be configured to disperse liquid feed 104 into small droplets, thereby maximizing an amount of liquid surface area exposed to heated gas 102. As one example, atomizer 105 may be configured for two-fluid atomization. Other atomizer configurations including, but not limited to, pressure atomization and rotary atomization, are considered within a scope of the present disclosure. Liquid feed 104 and heated gas 102 may enter drying chamber 106 at varied geometries. In one embodiment, heated gas 102 and liquid feed 104 may both enter at a top of drying chamber 106 in a co-current configuration. Further details with respect to a VSD system in the co-current configuration are discussed below with respect to FIG. 5. In an alternate embodiment, liquid feed 104 may enter the top of drying chamber 106 while heated gas 102 enters drying chamber 106 from a bottom of drying chamber 106 in a counter-current configuration. Further details with respect to a VSD system in the counter-current configuration are discussed below with respect to FIG. 6.

Operating parameters of VSD system 100 may be chosen such that interaction of heated gas 102 with the atomized droplets of liquid feed 104 results in evaporation of the liquid phase by the time the atomized droplets exit drying chamber 106. Operating parameters may include pressure within drying chamber 106, temperature at an outlet of drying chamber 106, temperature at an inlet of drying chamber 106, and a ratio of liquid feed 104 to heated gas 102. In examples where VSD system 100 is configured for co-current spray drying, adjusting the outlet temperature of drying chamber 106 has a greater impact on dried product quality than adjusting the inlet temperature of drying chamber 106. In examples where VSD system 100 is configured for counter-current spray drying, the adjusting inlet temperature of drying chamber 106 may have a greater impact on dried product quality than adjusting the outlet temperature of drying chamber 106. As described further below with respect to FIGS. 2-3 an effect of the operating parameters on a drying rate may be predicted by a model. In this way, operating parameters may be selected which result in a desired drying rate at a temperature which does not degrade the product. Additionally or alternatively, the model may be used to determine if modifying a size of drying chamber 106 is demanded for obtaining a dry product under achievable operating parameters.

The product may exit drying chamber 106 and may enter cyclone 108. Cyclone 108 may be configured to separate product particles 110 from the heated gas through vortex separation. Product particles 110 may be collected from an outlet of cyclone 108. Vacuum 112 may be fluidly coupled to drying chamber 106 via cyclone 108. In this way, vacuum 112 may evacuate drying chamber 106 and thereby reduce an operating pressure within drying chamber 106. Sizing of cyclone 108, positioned between vacuum 112 and drying chamber 106, may be chosen based on a desired operating pressure of VSD 100. In one example, a larger cyclone 108 may reduce a pressure drop between an inlet of cyclone 108 and an outlet of cyclone 108 and a load on vacuum 112 may be decreased. Dimensions of cyclone 108 are discussed further below.

Other modifications to a VSD system such as VSD 100 have been concerned with enhancing transfer of heat from a heated gas to a liquid feed under vacuum conditions in order to improve a throughput. However, in such systems, the temperature experienced by some products may be high enough to degrade the product. Instead, operating conditions and VSD system design may be chosen such that the product may be dried at an acceptable rate at a temperature below the boiling point of the liquid phase of the liquid feed. Operating conditions may include drying chamber pressure, outlet temperature and ratio of liquid feed to drying gas. VSD system design may include a co-current or counter current geometry, a size of a drying chamber and a size of cyclone.

A model of droplet drying within a drying chamber (such as drying chamber 106 of FIG. 1) may be illustrated by illustration 200 of FIG. 2. A droplet 202 may include a liquid feed drop 204. Liquid feed drop 204 may be surrounded by heated gas 206. Heat transfer between heated gas 206 and liquid feed drop 204 may occur at interface 208. In one example, first droplet 202 may be a droplet at a top of a drying chamber at a beginning of a drying process. Arrow 214 may indicate a lapse of drying time and passage of droplet 202 through a drying chamber. After an amount of drying time, interface 208 may recede and liquid feed drop 204 may be smaller. The speed at which interface 208 recedes may be referred to as interface velocity which may be proportional to a drying rate. Interface velocity is given by equation 1 below.

$$\text{interface velocity} = \frac{2\,k_m P_{dryer}}{c_l R T_s}\,\frac{\frac{P_{sat}(T_s)}{P_{dryer}} - x_\infty}{1 - \frac{P_{sat}(T_s)}{P_{dryer}}} \tag{1}$$

$k_m$ is the mass transfer coefficient which is a function of a liquid feed drop velocity and diameter, $c_1$ is the concentration of solvent in the liquid phase, $P_{sat}(T_s)$ is the saturation pressure of the solvent as a function of the surface temperate of the liquid feed drop ($T_s$), $P_{dryer}$ is the total pressure in the spray dryer, $x_\infty$ is the solvent mole fraction at an outlet of the drying chamber, and R is the ideal gas constant.

The surface temperature of the liquid feed drop may depend on physical properties of the liquid phase and operating parameters of the VSD system. The surface temperature of the liquid feed drop may be calculated from a mass and energy balance at interface 208 that leads to equation 2 below.

$$\frac{hRT_s}{k_m P_{dryer}\Delta H_{vap}} = \frac{\frac{P_{sat}(T_s)}{P_{dryer}} - x_\infty}{(T_{out} - T_s)\left(1 - \frac{P_{sat}(T_s)}{P_{dryer}}\right)} \tag{2}$$

h is the heat transfer coefficient which is a function of liquid feed drop velocity and diameter, $\Delta H_{vap}$ is the enthalpy of vaporization of the liquid phase, and Tour is the outlet temperature of the drying chamber. $\Delta H_{vap}$ may be approximated as a constant for the ranges of temperatures and pressures under which spray drying occurs. In some examples, equation 2 may be used to calculate the surface temperature of the liquid feed drop where the VSD system is configured as a co-current spray dryer. In alternate examples, where the VSD system is configured in counter-current mode, inlet temperature may also influence the surface temperature of the liquid feed drop. In such examples, $T_{out}$ in equation 2 may be replaced with an average of inlet temperature ($T_{in}$) and $T_{out}$ to calculate the surface temperature of the liquid feed drop where the VSD system is configured as a counter-current spray dryer.

Equations 1 and 2 may assume that compositions a liquid phase of liquid feed drop 204 and heated gas 206 are in equilibrium at interface 208. Additionally, equations 1 and 2 assume that the liquid feed drop is pure liquid phase (e.g., no product is suspended/dissolved in the liquid phase). When a product is present within liquid feed drop 204, as interface 208 recedes, a shell 212 of the product may form at a surface of liquid feed drop 204. For this reason, equations 1 and 2 may not be able to a priori predict a drying rate when a liquid feed includes a product. However, the relative effects on drying rate by adjusting the outlet temperature ($T_{out}$) and pressure inside the drying chamber (e.g., dryer chamber) ($P_{dryer}$) may be the same whether or not the liquid phase includes the product. In this way, operational parameters at reference conditions including a given liquid to gas ratio resulting in a minimum drying rate may be empirically determined and a model including equations 1 and 2 may be used to calculate a range of adjusted conditions including $T_{out}$ and $P_{dryer}$ which may also achieve the same rate. By calculating parameters with respect to a relative rate change as described above, the model may include an approximation for droplet solidification. Said another way, the model describes liquid evaporation from a droplet as an approximation for droplet drying kinetics. By capturing droplet drying kinetics, further approximations may be made related to droplet solidification.

An example of a graph 300 showing relative drying rate as a function of outlet temperature at different pressures is shown in FIG. 3. Graph 300 may correspond to a liquid to gas mass ratio of 0.016 wherein the liquid feed is water and a product is included at a desired concentration. Reference spray drying parameters may be chosen which result in a tolerable drying rate for a liquid feed and liquid to gas mass ratio. For example, an ambient pressure of 0.9 bar and an outlet temperature of 35° C. may result in a tolerable drying rate when the liquid phase to gas ratio is 0.016. In one embodiment, the reference spray drying parameters may be chosen based on experiments performed using a short form spray dryer. In alternate embodiments, the reference spray drying parameters may be chosen based on prior knowledge of the spray drying process. The tolerable drying rate may be a minimum drying rate ($R_{min}$), below which the product may stick to walls of a drying chamber (e.g., drying chamber 106 of FIG. 1) instead of exiting the drying chamber as dried particles. In another example, $R_{min}$ may be a rate at which a percent yield of particles exiting the drying chamber during steady state continuous operation is at or above a minimum percent yield. The minimum percent yield may depend on an identity and quantity of the product. In one embodiment, the percent yield at $R_{min}$ may be greater than 50%. In an alternate embodiment, the percent yield at $R_{min}$ may be greater than 70%. The tolerable drying rate may be set to 1.0 on a scale of relative drying rate shown on a y-axis of graph 300 and corresponding to line 302.

Using equations 1 and 2, relative drying rates as a function of $T_{out}$ for different drying chamber pressures may be calculated. Plot 304 corresponds to an ambient pressure of 0.9 bar, plot 306 corresponds to a pressure of 0.5 bar, plot 308 corresponds to a pressure of 0.1 bar, and plot 310 corresponds to a pressure of 0.05 bar. As shown by graph 300, a relative drying rate of 1.0 may be reached at a lower $T_{out}$ as pressure within the drying chamber is decreased. For example, plot 308 indicates that a relative drying rate of 1.0 may be achieved at a $T_{out}$ of 11° C. A minimum dryer chamber pressure may be limited by an available pump size. For example, a practical minimum pressure of 0.05 bar may be achieved within the drying chamber for a commercial scale VSD system. In this way a $P_{dryer}$ may be selected for which $T_{out}$ does not exceed an upper temperature threshold ($T_{max}$) of the product.

Additionally, a tall form spray dryer or a counter-current spray drying configuration may be used to increase a residence time of the particles within the drying chamber. In this way a decreased relative drying rate (e.g., <1.0) may be tolerable. As one example, a height of the drying chamber may be increased by a factor of two over the drying chamber height of the short form dryer. As one example, for the same L/G ratio, a relative drying rate of 0.4 (shown by line 312 on graph 300) may be determined to be a minimum drying rate for a tall spray dryer or a counter current spray dryer. As shown by plot 304, $T_{out}$ may be decreased from 35° C. to 25° C. when a tolerable relative drying rate decreases to 0.4. However, reconfiguring the spray drying system by increasing the drying chamber height or spray drying in a counter-current configuration may be limited by practical considerations when transferred to the commercial scale VSD system. For this reason, decreasing the drying chamber pressure may be preferred over increasing the drying chamber height. In this way, graph 300 may be used to select the drying chamber pressure and the drying chamber height based on a desired $T_{out}$ for a water liquid phase at a liquid to gas mass ratio of 0.016.

Turning now to FIG. 5, a schematic of a VSD system 500 in a co-current configuration is shown. VSD system 500 may include a liquid feed 502 and a heated gas 504. Liquid feed 502 may include a product and a liquid phase and may be similar to liquid feed 104 of FIG. 1. Heated gas 504 may be nitrogen gas and may be similar to heated gas 102 of FIG. 1. Gas may be removed from VSD system 500 by vacuum pump 524. In one example $P_{dryer}$ may be controlled by a feed rate of heated gas 504 into a drying chamber 506. Liquid feed 502 may be atomized using a liquid atomizer and may be introduced through a top (e.g., with respect to a gravitational axis) of drying chamber 506. Different methods of atomization are considered within a scope of the present disclosure, and may include conventional pressure atomization, two-fluid atomization, and rotary atomization as well as other unconventional methods of atomization. Heated gas 504 may also be introduced through the top of drying chamber 506. Heated gas 504 and liquid feed 502 may travel in the same direction downward through drying chamber 506. In this way, a temperature experienced by the product may be minimized. However, heated gas 504 may also drive product particles towards a bottom of the drying chamber, thus decreasing a residence time of the product inside drying chamber 506 and thereby increasing a demanded $T_{out}$ and $P_{dryer}$ to achieve $R_{min}$. In some examples, VSD system 500 may be configured to include a tall form drying chamber 506 to increase the residence time of product inside drying chamber 506.

In some examples, drying chamber 506 may be a jacketed drying chamber, including a jacket 507 fluidly coupled to a temperature control bath 509. Jacket 507 and temperature control bath 509 may be similar to jacket 107 and temperature control bath 109 of FIG. 1. Fluid at a temperature controlled by the temperature control bath may circulate through jacket 507 and enable active control of a temperature of drying chamber 506. In this way, influence of environmental temperature on the temperature of drying chamber 506 may be minimized.

An output of drying chamber 506 may be fed into an inlet of cyclone 512. Cyclone 512 may be configured to separate desired product particles from exhaust gas and fine dust (e.g., particles<5 μm in diameter). A product isolation valve 508 may be positioned between a bottom outlet of cyclone 512 and a removable product collection chamber 510. When product isolation valve 508 is in an open position, desired product particles may flow into removable product collection chamber 510 and both cyclone 512 and removable product collection chamber 510 may be under vacuum. When product isolation valve 508 is in a closed position, removable product collection chamber 510 may be brought to atmospheric pressures and emptied while cyclone 512 remains under vacuum. In this way, product may be collected without halting operation or breaking a vacuum of the remaining components of VSD system 500.

Fine dust and exhaust gas may exit through a top of cyclone 512 and pass through filter 514. Filter 514 may be configured to collect fine dust and allow exhaust gas to pass through. VSD system 500 may optionally include a liquid trap system positioned within box 515 of FIG. 5. The liquid trap system may include a heat exchanger 516 fluidly coupled to a chiller 518. Heat exchanger 516 may receive hot exhaust gas from filter 514 and pass the hot exhaust gas over a component cooled by chiller 518. Liquid from hot exhaust gas may condense on the cold component as the hot exhaust gas cools and the condensate at a bottom of heat exchanger 516. The cooled exhaust may then enter vacuum pump 524. Cooling exhaust gas may densify the exhaust gas before it enters vacuum pump 524, thereby making vacuum pump 524 more efficient and lowering a $P_{min}$ of VSD system 500. Increasing vacuum pump efficiency this way may be more significant as a scale of VSD system (e.g., larger spray dryer and larger vacuum pump) increases. Additionally, moisture within the exhaust gas may condense upon cooling the exhaust gas in heat exchanger 516 and liquid exhaust 522 may be pumped from a bottom of heat exchanger 516 by liquid pump 520. Removing liquid exhaust 522 from exhaust gas before reaching vacuum pump 524 may be desirable if vacuum pump 524 is not tolerant to the presence of moisture.

Exhaust gas may be pulled out by vacuum pump 524 and leave vacuum pump 524 as exhaust 526. Exhaust 526 may include both moisture from the liquid phase and heated gas 504. Vacuum pump 524 may include a gas ballast 525. Gas ballast 525 may allow moisture entering vacuum pump 524 with the exhaust gas to be purged with exhaust 526. Gas ballast 525 may be opened more often if VSD system 500 does not include liquid trap system 515.

Turning now to FIG. 6, a schematic of a VSD system 600 in a counter-current configuration is shown. VSD system 600 may include similar components to VSD system 500 such as cyclone 512 and vacuum pump 524. Similar components are numbered the same as in FIG. 5 and are not reintroduced.

Liquid feed 502 may be atomized by a liquid atomizer and introduced to drying chamber 506 through the top and may travel downwards through drying chamber 506 by action of gravity. Herein, liquid atomization by both conventional configurations (e.g., two-fluid atomization, pressure atomization, rotary atomization, etc.) and unconventional configurations are considered. Heated gas 504 may be introduced to drying chamber through a side of a bottom (with respect to gravity) portion of drying chamber 506 and may be directed upwards to the top of drying chamber 506. In this way, the atomized liquid droplets may be spaced away from the top of drying chamber 506 before interacting with heated gas 504. Upon interacting with heated gas 504 moving upward, a path of the atomized droplets may be directed back towards the top of drying chamber 506. In this way, a residence time of atomized liquid droplets within drying chamber 506 may be increased. When residence time is increased, a shorter drying chamber may be chosen for a selected $T_{out}$ and $P_{dryer}$.

VSD system 600 may include a chamber particle isolation valve 602 and chamber product collection chamber 604. Chamber particle isolation valve 602 and chamber product collection chamber 604 may be positioned at a lowest point of drying chamber 506 with respect to gravity and may be used similarly to product isolation valve 508 and removable product collection chamber 510. Larger particle products which may fall out of the upward stream of heated gas 504 may be collected from the bottom of drying chamber 506 through an open chamber particle isolation valve 602 and chamber product collection chamber 604 may be fluidly isolated from VSD system 600 when chamber particle isolation valve 602 is in a closed position. Smaller product particles may be carried out of a top side of drying chamber 506 and directed towards cyclone 512. Components positioned downstream of drying chamber 506 may be configured similarly to VSD system 500.

In some examples, chamber particle isolation valve 602 and chamber product collection chamber 604 may be omitted and heated gas 504 may enter drying chamber 506 from the lower point of drying chamber 506 with respect to gravity. In such an example, particles may be collected in removable product collection chamber 510. In this way, a total number of parts of VSD system 600 may be reduced thereby reducing system complexity and cost.

A cyclone such as cyclone 512 of FIGS. 5-6 and cyclone 108 of FIG. 1 may be selected for use in a VSD system such as VSD system 100, VSD system 500, and/or VSD system 600. In addition to considering how well the cyclone may work to separate particle products from exhaust gasses, the cyclone may be fluidly coupled to both a drying chamber and a vacuum. For this reason, a pressure drop between an outlet of the cyclone and an inlet of a cyclone may effect a pressure inside the drying chamber. For an equivalent mass flow rate, a cyclone included in a spray drying system operating under atmospheric pressure may incur a smaller relative pressure drop than a cyclone included in a VSD system. Said another way, the pressure drop incurred in cyclone positioned in a VSD system may be a greater percentage of overall system pressure than in a spray drying system under atmospheric pressure. For this reason, a size of the cyclone included in the VSD system may be increased when compared with an equivalent spray drying system operating under atmospheric pressure. As one example, increasing the cyclone size may include increasing a maximum diameter of the cyclone and a size of additional cyclone components (e.g., height, inlet diameter and outlet diameter) may be increased in size proportionally to the increased maximum diameter. Table 1 below gives examples of pressure of effect of cyclone pressure drop on other spray dryer system properties assuming pressure drop across the filter is negligible.

TABLE 1

Example drying chamber pressures for different cyclone pressure drops and different vacuum pump pressures.

| | Drying Chamber Pressure (mbar) | Cyclone Pressure Drop (mbar) | Pressure at Vacuum Pump (mbar) |
|---|---|---|---|
| Example A | 100 | 50 | 50 |
| Example B | 100 | 10 | 90 |
| Example C | 1000 | 50 | 950 |
| Example D | 1000 | 10 | 990 |

Comparing example A to example B, for an equivalent drying chamber pressure, a pressure at the vacuum pump may be lowered from 90 mbar to 50 mbar (approximately 40% decrease) when the cyclone pressure drop increases from 10 mbar to 50 mbar. Decreasing a pressure at the vacuum may demand a larger capacity vacuum pump. Additionally, cyclone pressure drop is also increased from 10 mbar to 50 mbar in comparing example C and D. However, for examples C and D, spray drying pressure is held at 1000 mbar. At a higher drying chamber pressure, the demanded change in pressure at the vacuum between examples C and D may be relatively small (e.g., approximately 4% decrease). Such a relationship is a consequence of the ideal gas law which dictates that a volumetric flow rate is inversely proportional to absolute system pressure.

As another example, a mass flow rate for a drying gas (e.g., heated gas 504) may be selected based on a desired drying rate (e.g., $R_{min}$) however, performance of cyclone, including collection efficiency and pressure drop may be based on volume flow rates. Decreasing a drying chamber pressure for a constant mass flow rate may result in a different volume flow rate and vice versa. For this reason, tuning a size of a cyclone such that collection efficiency is balanced with pressure drop is demanded for a VSD system.

Figure 7:
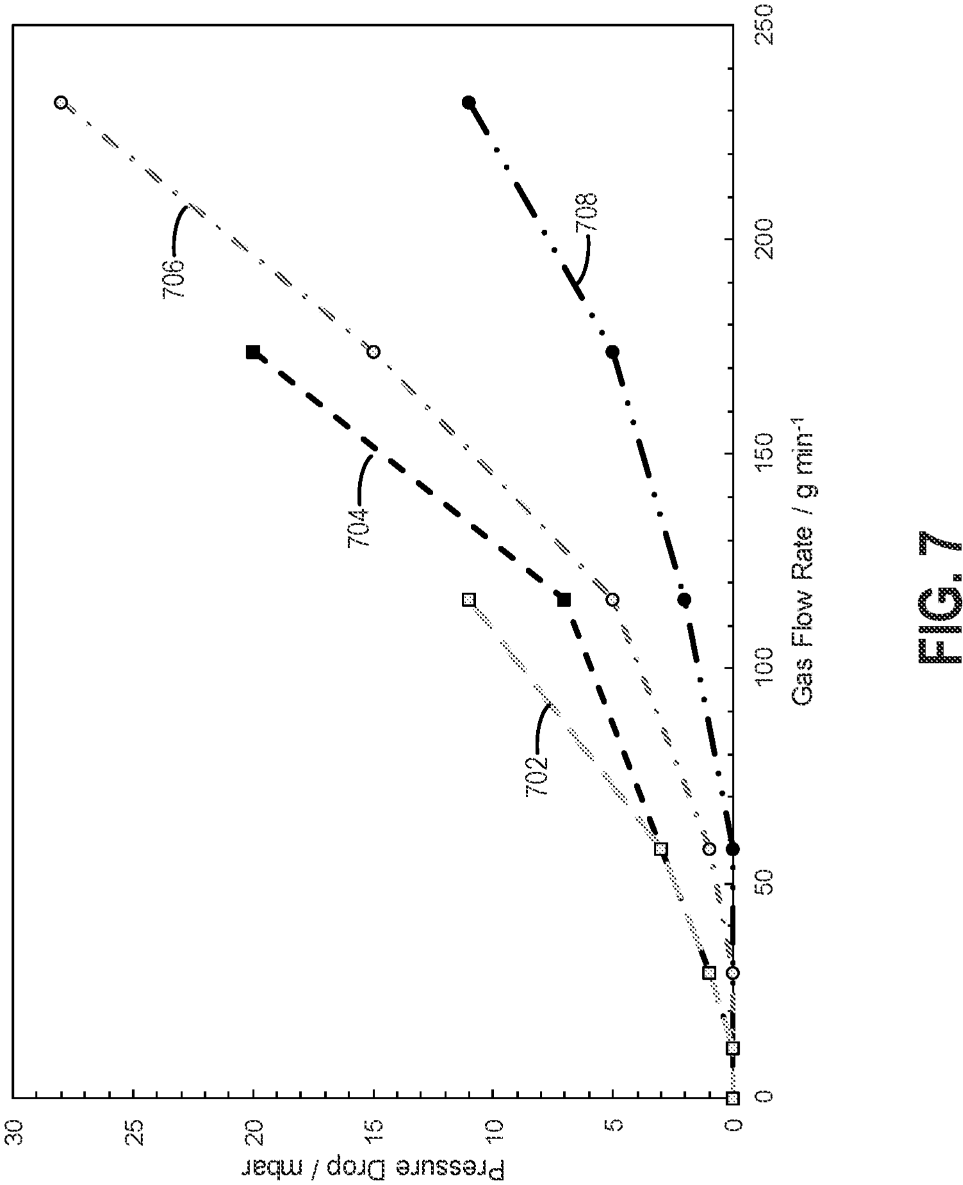
FIG. 7 shows a graph of pressure drop as a function of gas flow rate for a cyclone having a two-inch diameter.
Figure 7:
Figure 8:
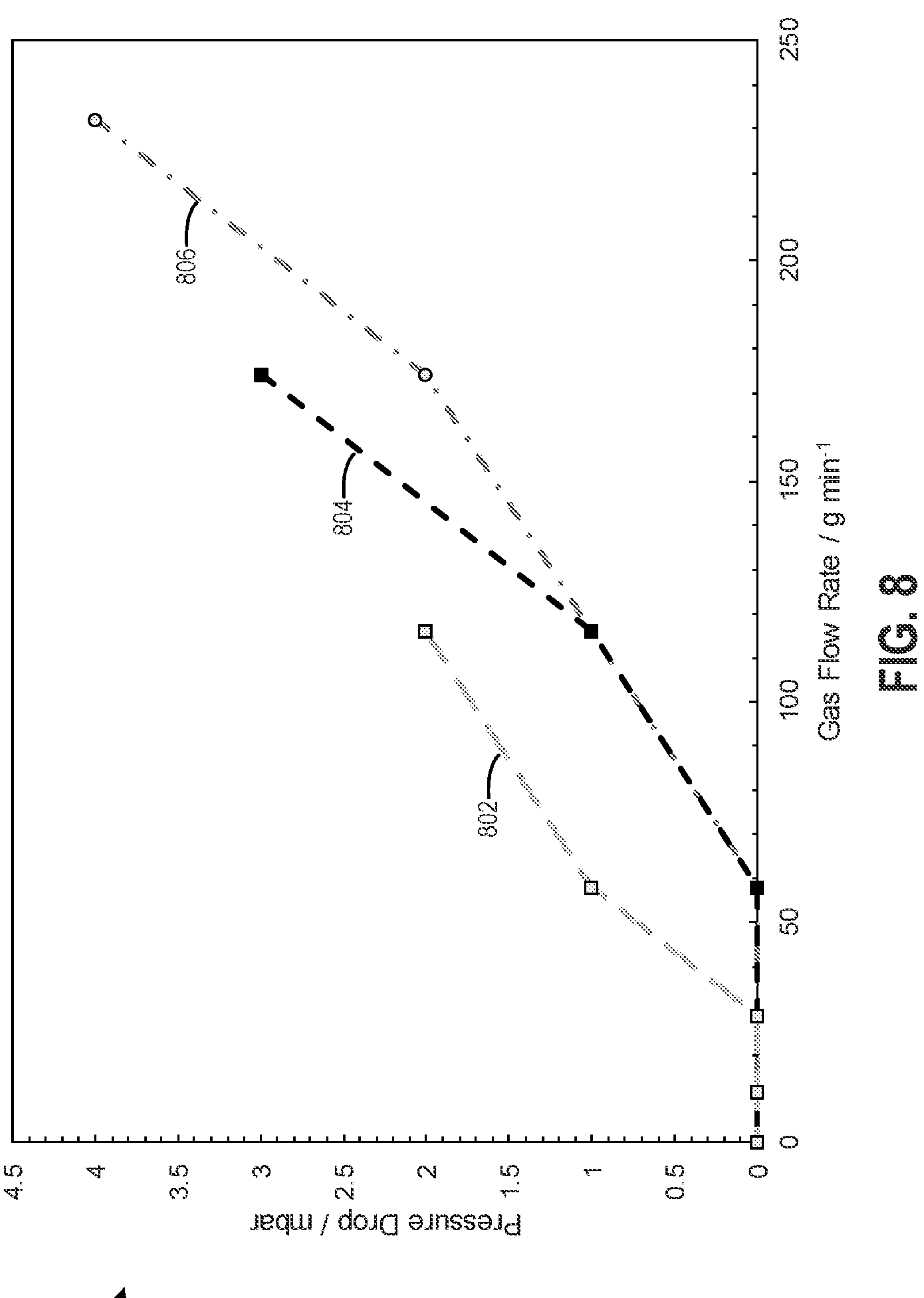
FIG. 8 shows a graph of pressure drop as function of gas flow rate for cyclone having a three-inch diameter.

Turning now to FIGS. 7 and 8, they further show the effects of drying chamber pressure and cyclone size on a pressure drop across the cyclone. FIG. 7 includes a graph 700 of a pressure drop as a function of gas flow rate for a cyclone having a 2" diameter and FIG. 8 includes a graph 800 pressure drop as function of gas flow rate for a cyclone having a 3" diameter. Plot 702 of FIG. 7 corresponds to a chamber pressure of 183 mbar, plot 704 corresponds to a chamber pressure of 263 mbar, plot 706 corresponds to a chamber pressure of 359 mbar and plot 708 corresponds to a chamber pressure of 900 mbar. For a given gas flow rate, comparison of plots 702, 704, 706, and 708 shows that a pressure drop across the cyclone increases as the chamber pressure decreases.

A similar trend of increasing pressure drop with decreasing chamber pressure is seen in graph 800 of FIG. 8. Graph 800 includes a plot 802 corresponding to a chamber pressure of 184 mbar, a plot 804 corresponding to chamber pressure of 252 mbar, and a plot 804 corresponding to chamber pressure of 338 mbar. Additionally, comparing plots of graph 800 and graph 700, for around the same gas flow rate and comparable chamber pressure (e.g., plots 702 and plot 802) the two-inch cyclone pressure drop shown in graph 700 is larger than the corresponding pressure drop shown in graph 800.

While increasing a size of a cyclone may decrease an effective pressure at a vacuum pump, smaller cyclones may collect dried product more efficiently than larger cyclones. Selecting a cyclone for a VSD system may include balancing a demand for a cyclone collection efficiency with reducing a pressure drop across the cyclone. Methods of selecting a cyclone for a VSD system are discussed further below with respect to FIGS. 4A-4B.

Figure 4A:
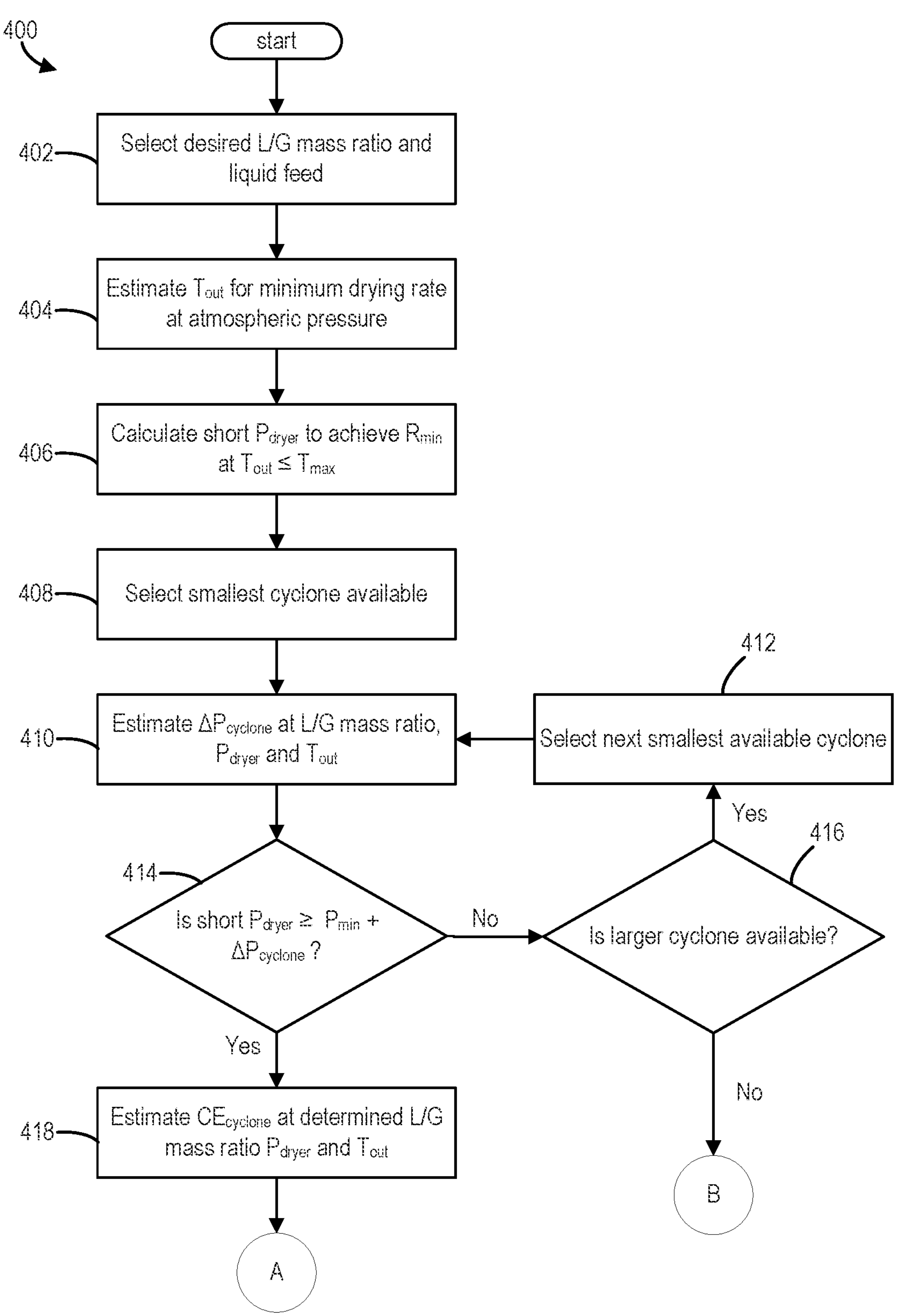
FIG. 4A shows a flow chart of an example of a method for determining drying chamber outlet temperature and drying chamber pressure.
Figure 4B:
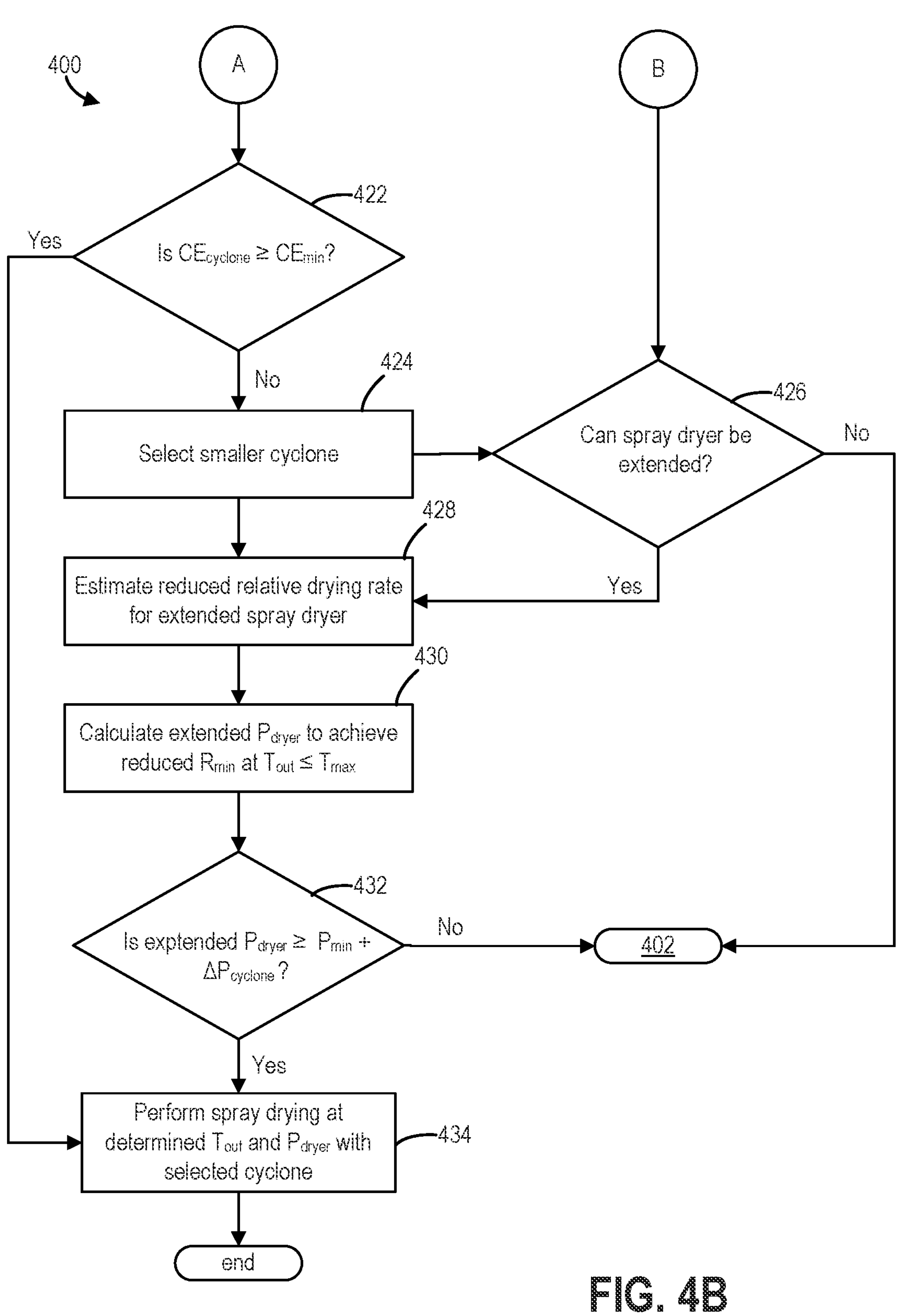
FIG. 4B shows a flow chart of a continuation of the method shown in FIG. 4A.

A flow chart of an example of a method 400 for selecting a drying chamber pressure ($P_{dryer}$) and drying chamber height for a VSD system is shown in FIGS. 4A and 4B. The VSD system may be similar to VSD system 100 shown in FIG. 1. Further, the VSD system may be configured as co-current system such as VSD system 500 of FIG. 5 or as a counter-current system such as VSD system 600 of FIG. 6. Additionally, method 400 may include estimating parameters based on experiments using a reference spray dryer. In one example, the reference spray dryer may be a short form bench scale spray dryer operating at atmospheric pressure in a co-current configuration. Further, parameters may be estimated based on an extended spray drying system. The extended spray drying system may be configured to increase a residence time of particles within the drying chamber. For example, the extended spray drying system may be configured as a counter-current spray dryer or a height of the drying chamber may be increased. The extended spray dryer may be operated under atmospheric pressure.

The VSD system may be used for spray drying a temperature sensitive product suspended or dissolved in a liquid phase as described above with respect to the product of liquid feed 104 of FIG. 1. The product may be characterized by a maximum temperature ($T_{max}$) above which the product may begin to degrade. In this way, $T_{max}$ may depend on the product being spray dried. In some examples $T_{max}$ may be less than a boiling point of the liquid phase. Further, $T_{max}$ may be 5° C. less than the boiling point of the liquid phase. In some examples, the liquid phase may include a mixture of solvents, each solvent of the mixture having a different boiling point, and the $T_{max}$ may be less than (e.g., 5° C. less than) a boiling point of a majority of the liquid phase. Herein, the majority of the liquid phase refers to greater than or equal to 50% by volume of the liquid phase). In some examples the product may be an API and $T_{max}$ may be a degradation temperature of the API. Above the degradation temperature, the API may degrade and lose effectiveness as an active ingredient in a pharmaceutical formulation. Method 400 may enable a user to select operating parameters (e.g., $P_{dryer}$, $T_{out}$, drying chamber height, co-current or counter-current configuration, liquid phase, and liquid to gas ratio) which may enable spray drying the product at or above a minimum rate ($R_{min}$). The minimum rate may be the rate below which the product may stick to walls of the drying chamber instead of exiting the drying chamber as particles and a minimum percent yield of the product is obtained as described above with respect to FIG. 3.

At 402, method 400 includes selecting a desired liquid to gas mass ratio and liquid feed. The liquid to gas mass ratio (L/G mass ratio) may be controlled by selecting a liquid feed rate and a heated gas feed rate. The liquid feed may be similar to liquid feed 104 of FIG. 1 and may include a liquid phase and a product at a desired concentration. The desired concentration may be selected based on physical characteristics of the product in the liquid phase (e.g., solubility, viscosity, and/or stability in the liquid phase) and a demanded throughput of the method. As one example, the concentration of the product in the liquid phase may be between 0.1% and 30% by weight. The liquid phase may be selected based on solubility properties and compatibility of the product. For example, a product including nucleic acids may be compatible with a majority aqueous liquid phase while an amorphous solid dispersion may be compatible with a majority organic liquid phase.

At 404, method 400 includes estimating the reference $T_{out}$ demanded to result in $R_{min}$ for the selected L/G mass ratio at atmospheric pressure for a reference spray dryer configuration. In one example, $T_{out}$ and $R_{min}$ may be determined experimentally (e.g., empirically) by spray drying using the liquid feed and L/G ratio selected at 402 using a reference spray drying system. In one example, the reference spray drying system may be a short form spray dryer configured as a co-current spray dryer used in a laboratory setting.

At 406, method 400 includes calculating a predicted dryer pressure ($P_{dryer}$) to achieve $R_{min}$ at a $T_{out}$ less than or equal to $T_{max}$. As one example $T_{max}$ may be <35° C., <25° C., <15° C., or <6° C. As a further example, when the liquid phase includes a low volatility organic solvent, $T_{max}$ may be <80° C., <70° C., or <60° C. Further, $T_{max}$ may be less than a boiling point of the liquid phase or less than a boiling point of a majority of the liquid phase in examples where the liquid phase is a blend of different solvents. As one example, $P_{dryer}$ may be less than ambient pressure by 0.05 bar. In further examples, $P_{dryer}$ may be less than or equal to 0.8 bar or $P_{dryer}$ may be less than or equal to 0.5 bar. In alternate examples, $P_{dryer}$ may be in a range between 0.2 bar and 0.6 bar, a range between 0.05 bar to 0.6 bar, or in a range between 0.01 bar to 0.8, or in a range between 0.01 bar up to 0.05 bar below ambient pressure. $P_{dryer}$ and $T_{out}$ may be calculated using equations 1 and 2 as described above with respect to FIG. 2. The $R_{min}$ determined at step 404 may be proportional to a target interface velocity for the liquid feed and L/G mass ratio selected at 402. Relative changes to $R_{min}$ by adjusting $T_{out}$ and $P_{dryer}$ may be predicted using equations 1 and 2 without demanding prediction of an absolute drying rate.

At 408, method 400 includes selecting a smallest cyclone available. Selecting the smallest cyclone may include selecting, from the available cyclones, the cyclone having the highest cyclone collection efficiency of dried powder. Cyclone collection efficiency may refer to a ratio of mass of dried particles recovered from the cyclone to a total mass of dried particles exiting the drying chamber. Increasing cyclone collection efficiency may also increase an overall percent yield of dried product. As one example, a smallest available cyclone may have a diameter of 0.5".

At 410, method 400 includes estimating an increase in system pressure due to a pressure drop over the selected cyclone ($\Delta P_{cyclone}$) for the selected L/G mass ratio, $P_{dryer}$ and $T_{out}$. $\Delta P_{cyclone}$ cyclone may be defined as a difference in pressure between an inlet ($P_{in}$) and an outlet ($P_{out}$) of the cyclone ($P_{in}$-$P_{out}$). Pressure decreases in a direction of flow through the cyclone, therefore $\Delta P_{cyclone}$ is a positive value. $\Delta P_{cyclone}$ may be calculated based on physical dimensions of the cyclone and properties of the heated gas feed. Additionally or alternatively, $\Delta P_{cyclone}$ over the selected cyclone may be determined based on dynamic simulations or determined empirically by measuring pressure of the system immediately upstream and immediately downstream of the cyclone.

At 414, method 400 includes determining if $P_{dryer}$ determined at 406 is greater than or equal to a sum of $P_{min}$ and $\Delta P_{cyclone}$. $P_{min}$ may be a minimum dryer chamber pressure which may be realistically achieved within a drying chamber sized for commercial applications. $P_{min}$ may depend on $P_{vac}$. $P_{vac}$ may be a minimum pressure of a drying chamber fluidly coupled to the vacuum pump with no intervening components causing additional pressure drops. A size and/or power of vacuum pump (e.g., vacuum pump 524) included in the VSD system may determine $P_{vac}$. As one example $P_{vac}$ may be 0.05 bar. In another example $P_{vac}$ may be 0.01 bar. In further examples, $P_{vac}$ may be in a range of 0.01bar to 0.05 bar, or $P_{vac}$ may be greater than or equal to 0.01bar. $P_{min}$ may be increased by an amount determined a pressure drop across the cyclone ($\Delta P_{cyclone}$). Additionally or alternatively, $P_{min}$ may be decreased by including a heat exchanger placed downstream of the cyclone and upstream of the vacuum pump. As described above, a heat exchanger may densify gas exhaust before the gas exhaust reaches the vacuum pump, thereby increasing an efficiency of the vacuum pump. As one example, $P_{min}$ may be in a range of 0.05 bar to 0.6 bar. In alternate examples, $P_{min}$ may be in a range of 0.01 bar to 0.8 bar.

If $P_{dryer}$ is less than the sum of $P_{min}$ and $\Delta P_{cyclone}$, method 400 proceeds to 416 and includes determining if a larger cyclone is available. The larger cyclone may have a larger maximum diameter and a pressure drop across the larger cyclone may be less than a pressure drop across the small cyclone. Additionally, a $\Delta P_{cyclone}$ may decrease in magnitude as the cyclone size increases and a corresponding pressure drop across the cyclone decreases. If the larger cyclone is available, method 400 proceeds to 412 and includes selecting the next smallest available cyclone. The next smallest available cyclone may be larger than the currently selected cyclone. Method 400 then returns to 410 and includes determining $\Delta P_{cyclone}$ for the next smallest available cyclone for the L/G mass ratio, $P_{dryer}$ and $T_{out}$.

If the larger cyclone is not available, method 400 proceeds to 426 and determines if the spray dryer can be extended. If the spray dryer cannot be extended, method 400 returns to 402 and a new L/G mass ratio and/or liquid feed are selected. If the spray dryer can be extended, method 400 proceeds to 428 and includes estimating a reduced relative drying rate (reduced $R_{min}$) for the extended spray dryer. An extended spray dryer may be a spray dryer configured to increase a residence time of product within the drying chamber. As one example, an extended spray dryer may include a drying chamber with a height greater than the reference spray dryer. Further, the drying chamber of the extended spray dryer may be two times the height of a drying chamber of the reference spray dryer used to determine $R_{min}$. Further, an extended spray dryer may be configured as a counter-current spray dryer. Determining the reduced $R_{min}$ may include experimentally determining the reduced $R_{min}$ for the selected liquid feed and L/G ratio using a lab scale version of the extended spray dryer.

At 430, method 400 includes calculating an extended $P_{dryer}$ to achieve reduced minimum drying rate (e.g., reduced $R_{min}$) at a $T_{out}$ less than $T_{max}$. Extended $P_{dryer}$ may be calculated using equations (1) and (2) as described above. Because a residence time of the particle inside the drying chamber is increased from the reference spray dryer to the extended spray dryer, reduced $R_{min}$ may be less (e.g., slower) than $R_{min}$ thereby allowing extended $P_{dryer}$ to be greater than $P_{dryer}$. At 432, method 400 determines if extended $P_{dryer}$ is greater than or equal to $P_{min}+\Delta P_{cyclone}$. If extended $P_{dryer}$ is greater than or equal to $P_{min}+\Delta P_{cyclone}$, method 400 proceeds to 434 and spray drying is performed using the determined $T_{out}$ and extended $P_{dryer}$ resulting in the reduced $R_{min}$ and using the extended spray dryer configuration (e.g., counter-current configuration and/or increased drying chamber height). In some examples, spray drying the liquid feed may further include controlling a jacket temperature of a jacketed drying chamber. As one example the jacket may be similar to jacket 107 of FIG. 1 and the jacket temperature may be controlled by setting a temperature of a temperature control bath (e.g., temperature control bath 109 FIG. 1) fluidly coupled to the jacket. In this way processing temperatures, such as $T_{out}$ may be controlled with greater accuracy during spray drying of the liquid feed than without controlling a jacket temperature. In some examples, the product may be a pharmaceutical product and the spray dried pharmaceutical product may be included in a pharmaceutical formulation.

If at 432 it is determined that extended $P_{dryer}$ is less than $P_{min}+\Delta P_{cyclone}$, method 400 proceeds to 402 and a different liquid feed and/or L/G ratio are selected. As one example, a fraction of low volatility organic solvent in the liquid phase may be decreased. As an alternate example, the L/G ratio may be decreased.

Returning now to 414, if method 400 determines the short $P_{dryer}$ is greater than or equal to the $P_{min}+\Delta P_{cyclone}$, method 400 proceeds to 418 and includes estimating the cyclone collection efficiency ($CE_{cyclone}$) at the determined L/G mass ratio, $P_{dryer}$ and $T_{out}$. In some example $CE_{cyclone}$ may be determined experimentally using model systems. For example, a yield for a test spray wherein the liquid feed includes excipients and no API may be used to determine $CE_{cyclone}$, assuming all loss is due to the cyclone. Additionally or alternatively $CE_{cyclone}$ may be calculated based on physical properties of the cyclone and an expected median spray dried particle size. Method 400 then proceeds to 422 and includes determining if $CE_{cyclone}$ greater than or equal to a minimum acceptable collection efficiency ($CE_{min}$). In some examples, the $CE_{min}$ may be 80%. In further example $CE_{min}$ may be 97%. If method 400 determines that $CE_{cyclone}$ is greater than or equal to $CE_{min}$ method 400 proceeds to 434 and includes performing spray drying of the selected liquid feed at the selected L/G ratio and at the $T_{out}$ and $P_{dryer}$ determined to result in a drying rate of at least $R_{min}$ using a spray drying system configured as the reference spray drying system including the selected cyclone. If method 400 determines the $CE_{cyclone}$ is not greater than or equal to $CE_{min}$ method 400 proceeds to 424 and includes selecting a smaller cyclone if available. The smallest cyclone may have the largest collection efficiency. Selecting the smaller cyclone may increase a pressure drop across the cyclone and a magnitude of $\Delta P_{cyclone}$ may increase. For this reason, $P_{dryer}$ may no longer be greater than or equal to $P_{min}+\Delta P_{cyclone}$ and method 400 may proceed to 426 and include determining if the spray dryer can be extended. Method 400 may proceed as described above following the determination at step 426.

Method 400 ends following step 434 after spray drying of the product using the selected spray dryer and cyclone at the determine $T_{out}$ and $P_{dryer}$.

Examples of spray drying trehalose as an aqueous test solution including trehalose as a model test compound at a concentration of 14% by weight using a VSD (e.g., such as VSD 100 of FIG. 1) and a conventional spray drier (CSD) configured for different spray drying conditions at atmospheric pressure are shown in table 1 below. A batch size and atomization method in the VSD and conventional spray drier are kept substantially the same.

TABLE 1

Comparison of spray drying trehalose in vacuum and conventional spray driers

| | VSD | CSD-1 | CSD-2 | CSD-3 |
|---|---|---|---|---|
| $T_{in}$ (° C.) | 28 | 32 | 31 | 41 |
| $T_{out}$ (° C.) | 22 | 22 | 22.5 | 32 |
| L/G ratio | 0.013 | 0.0025 | 0.0026 | 0.013 |
| $P_{dryer}$ (bar) | 0.18 | 0.88 | 0.87 | 0.87 |
| Predicted relative saturation (%) | 12.5 | 11.8 | 12.4 | 3.4 |
| % Wet Yield | 65.9 | 45.4 | 42.6 | 66.2 |

Both the VSD and the CSD systems spray dried the trehalose test solution at a $T_{out}$ below a boiling point of water at the specified chamber pressure. $P_{dryer}$ of the VSD may be set by calculating a desired $P_{dryer}$ to achieve a minimum drying rate at the desired $T_{out}$ as described above with respect to FIGS. 4A-4B. For the same outlet temperature, the VSD was able to achieve comparable yields at an L/G ratio five times higher (e.g., five times higher throughput) than the CSDs. As further shown in table 1, in order to achieve a yield comparable to the VSD at a comparable L/G ratio, $T_{in}$ and $T_{out}$ are increased to 41° C. and 32° C. respectively. In examples where the product is not a model compound but an API with a $T_{max}$, increasing $T_{in}$ and $T_{out}$ may not be available. In examples where L/G ratio is lower (e.g., CS-1 and CS-2) the yield may be comparable to the VSD because an increased gas flow may be demanded to dry the same liquid feed faster. Spray drying using the VSD at a $P_{dryer}$ below atmospheric pressure may enable spray drying at a high % yield while avoiding other less desirable methods that increase gas flow, such as decreasing L/G or extending a spray dyer height or contact time.

As another example, shown in table 2 below, the 14% aqueous trehalose solution may be spray dried at different $P_{dryer}$ with other parameters remaining substantially the same.

TABLE 2

Comparison of VSD at different $P_{dryer}$

| | VSD-1 | VSD-2 | VSD-3 | VSD-4 |
|---|---|---|---|---|
| $T_{in}$ (° C.) | 48-50 | 46-50 | 47-50 | 48-50 |
| $T_{out}$ (° C.) | 19-20 | 19-20 | 19-20 | 19-21 |
| L/G ratio | 0.010 | 0.011 | 0.010 | 0.011 |
| $P_{dryer}$ (bar) | 0.365 | 0.352 | 0.297 | 0.29 |
| Predicted relative saturation (%) | 22.1 | 22.7 | 17.9 | 17.6 |
| % Wet Yield | 50.7 | 65.8 | 61.0 | 59.7 |

The % wet yield may vary based on uncontrollable system variability and not as a function of $P_{dryer}$. In this way, calculating a $P_{dryer}$ based on the modeling described above to achieve $R_{min}$ may select a maximum $P_{dryer}$. Achieving an actual $P_{dryer}$ less than the calculated $P_{dryer}$ amount may not affect the % yield, either negatively or positively. Calculating $P_{dryer}$ as described herein may allow a user to select an economical vacuum system that suits the intended purpose and is not more powerful than is demanded for little if any added benefit.

As a further example, shown below in table 3, trehalose is spray dried from aqueous solutions at two different concentrations and at different VSD configurations, some of which include cyclones of different diameters.

TABLE 3

Comparison of spray drying with different solutions using different cyclones.

| | VSD-1 | VSD-2 | VSD-3 | VSD-4 |
|---|---|---|---|---|
| wt. % trehalose | 14 | 14 | 4 | 4 |
| $T_{in}$ (° C.) | 14.5-14.9 | 15.1-15.4 | 15.1-15.8 | 16.0-164 |
| $T_{out}$ (° C.) | 14.1-15.2 | 14.1-15.2 | 13.5-15.5 | 13.8-15.5 |
| L/G ratio | 0.0102 | 0.0102 | 0.0946 | 0.0946 |
| $P_{dryer}$ (bar) | 0.304 | 0.328 | 0.339 | 0.331 |
| Cyclone dimeter (in.) | 3 | 2 | 3 | 2 |
| Predicted relative saturation (%) | 25.5 | 27.4 | 30.9 | 30.6 |
| % Wet Yield | 34.6 | 44.7 | 33.9 | 60.9 |

As shown in table 3, if an acceptable $P_{dryer}$ is achieved with a smaller cyclone diameter, a smaller cyclone diameter may improve a percent yield due to a higher cyclone collection efficiency of the smaller cyclone. Comparing VSD-1 and VSD-2, decreasing the cyclone diameter increases $P_{dryer}$. In some examples, such as comparing VSD-3 and VSD-4, a vacuum system may be adjusted to compensate for the larger pressure drop over the smaller cyclone. In such examples, especially if $P_{dryer}$ is close to a targeted $P_{dryer}$ based on the calculations of equation 1 and 2 as described above with respect to method 400, an increase in yield from the smaller cyclone may be greater than an increase in yield from the smaller cyclone when the vacuum system cannot be adjusted.

Additionally, the 14% trehalose liquid feed may be spray dried in a counter-current configuration (e.g., VSD 600 of FIG. 6), as shown in table 4 below.

TABLE 4

Results of spray drying in counter-current configuration

| | Counter-Current Ex. 1 | Counter-Current Ex. 2 |
|---|---|---|
| $T_{in}$ (° C.) | 36.5-39.6 | 53.8-54.2 |
| $T_{out}$ (° C.) | 20.4-21.0 | 20.0-20.3 |
| L/G ratio | 2.02 | 2.92 |
| $P_{dryer}$ (bar) | 0.338 | 0.339 |
| Predicted relative saturation (%) | 19.0 | 27.9 |
| % Wet Yield | 54.0 | 52.6 |

As described above, $T_{in}$ may have a larger effect on resulting particle yield and characteristics than $T_{out}$ when spray drying in a counter-current configuration. As shown in table 4, $T_{in}$ is increased between example 1 and example 2 and L/G ratio is also increased. In this way, a higher throughput may be possible if $T_{in}$ is increased while still observing wet yields of greater than 50%.

The technical effect of method 400 is to select a $P_{dryer}$ and $T_{out}$ for spray drying under at $T_{out}$ less than $T_{max}$. Spray dryer configuration and operational parameters may be chosen which include an approximation for droplet solidification and may result in an acceptable drying rate without causing thermal damage to the product. In this way, time and labor demanded to get to a successful temperature sensitive spray dried product may be decreased. Further, demand for a tall drying chamber of counter-current configuration may be determined. Additionally, $P_{min}$ of a VSD may be decreased by increasing a size of a cyclone. In this way, demand for a tall drying chamber or counter-current configuration may be avoided.

The disclosure also provides support for a method of spray drying, comprising: estimating an outlet temperature to achieve a minimum drying rate at an atmospheric pressure based on a selected liquid feed and a selected liquid to gas ratio, calculating a predicted dryer pressure at which the minimum drying rate can be reached at a reduced outlet temperature, wherein the reduced outlet temperature is less than a maximum temperature, and wherein the predicted dryer pressure includes an approximation for droplet solidification, and spray drying the selected liquid feed at the selected liquid to gas ratio, the predicted dryer pressure, and the reduced outlet temperature. In a first example of the method, the selected liquid feed includes a liquid phase and a product. In a second example of the method, optionally including the first example, the maximum temperature depends on the product included in the liquid phase. In a third example of the method, optionally including one or both of the first and second examples, the reduced outlet temperature is less than a boiling point of the liquid phase at the predicted dryer pressure. In a fourth example of the method, optionally including one or more or each of the first through third examples, the product is an active pharmaceutical ingredient. In a fifth example of the method, optionally including one or more or each of the first through fourth examples, estimating the reduced outlet temperature includes experimentation using a reference spray drying system. In a sixth example of the method, optionally including one or more or each of the first through fifth examples, the predicted dryer pressure in a range between 0.01 bar up to 0.05 bar below ambient pressure. In a seventh example of the method, optionally including one or more or each of the first through sixth examples, spray drying the selected liquid feed further includes controlling a jacket temperature of a jacketed drying chamber. In a eighth example of the method, optionally including one or more or each of the first through seventh examples, a minimum dryer chamber pressure is decreased by a heat exchanger placed downstream of a cyclone and upstream of a vacuum pump or increasing a size of the cyclone. In a ninth example of the method, optionally including one or more or each of the first through eighth examples, the selected liquid feed includes water and the maximum temperature is <35° C., <25° C., 15° C., or <6° C. or the selected liquid feed includes a low volatility organic solvent and the maximum temperature is <80° C., <70° C., or <60° C. In a tenth example of the method, optionally including one or more or each of the first through ninth examples, spray drying at the minimum drying rate includes spray drying in a spray drying system configured as a reference spray drying system and spray drying at a reduced minimum drying rate includes spray drying in a spray drying system configured as an extended spray drying system.

The disclosure also provides support for a vacuum spray drying system comprising: a liquid feed and a gas feed fluidly coupled to a drying chamber, a cyclone fluidly coupled to the drying chamber and configured to receive a dried product, a vacuum pump coupled to the drying chamber via the cyclone, and, wherein a height of the drying chamber, a size of the cyclone, and a power of the vacuum pump are determined by a model relating a minimum drying rate at reference conditions to a minimum rate at adjusted conditions. In a first example of the system, the adjusted conditions include a dryer pressure below atmospheric pressure and an outlet temperature less than a boiling point of a majority of the liquid feed at the drying chamber pressure. In a second example of the system, optionally including the first example, the liquid feed and gas feed are coupled to the drying chamber in a co-current or counter-current configuration. In a third example of the system, optionally including one or both of the first and second examples, the minimum drying rate is a rate corresponding to a percent yield at steady state continuous operation of greater than 50%.

The disclosure also provides support for a pharmaceutical formulation spray dried by a process of: selecting a liquid to gas mass ratio and liquid feed, the selected liquid feed including an active pharmaceutical ingredient and a liquid phase, estimating an outlet temperature to achieve a minimum drying rate at an atmospheric pressure based on a selected liquid feed and a selected liquid to gas ratio, calculating a predicted dryer pressure at which the minimum drying rate can be reached at a reduced outlet temperature, wherein the reduced outlet temperature is less than a degradation temperature of the active pharmaceutical ingredient, and wherein the predicted dryer pressure includes an approximation for droplet solidification, and spray drying the selected liquid feed at the selected liquid to gas ratio, the predicted dryer pressure, and the reduced outlet temperature. In a first example of the system, the active pharmaceutical ingredient is a protein, nucleic acids, a self-assembled nanoparticle, or small molecule. In a second example of the system, optionally including the first example, the reduced outlet temperature is below a boiling point of a majority of the liquid phase at the predicted dryer pressure. In a third example of the system, optionally including one or both of the first and second examples, spray drying at the reduced outlet temperature includes spray drying at <35° C., <25° C., or <15° C. when a majority of the liquid phase is aqueous. In a fourth example of the system, optionally including one or more or each of the first through third examples, spray drying at the reduced outlet temperature includes spray drying at <80° C., <70° C., or <60° C. when a majority of the liquid phase is a low volatility organic solvent.

In an alternate embodiment, the disclosure provides support for a method of spray drying, comprising: calculating a predicted dryer pressure at which a minimum drying rate for a selected liquid feed and liquid to gas ratio can be reached at an outlet temperature, wherein the outlet temperature is less than a maximum temperature, comparing the predicted dryer pressure to a minimum dryer chamber pressure, wherein the minimum dryer chamber pressure is determined by a vacuum pump size and a cyclone size, estimating a reduced minimum drying rate if the predicted dryer pressure is less than the minimum dryer chamber pressure, wherein the reduced minimum drying rate is reduced by extending a residence time of a product in a drying chamber, and spray drying the selected liquid feed at the selected liquid to gas ratio, the predicted dryer pressure, and the outlet temperature at the minimum drying rate or the reduced minimum drying rate. In a first example of the method, spray drying the selected liquid feed further includes controlling a jacket temperature of a jacketed drying chamber. In a second example of the method, optionally including the first example, the minimum dryer chamber pressure is greater than or equal to 0.01 bar. In a third example of the method, optionally including one or both of the first and second examples, extending the residence time of the product includes selecting an increased drying chamber height or spray drying in a counter-current configuration. In a fourth example of the method, optionally including one or more or each of the first through third examples, the minimum dryer chamber pressure is decreased by a heat exchanger or increasing the cyclone size. In a fifth example of the method, optionally including one or more or each of the first through fourth examples, the selected liquid feed includes water and the maximum temperature is <35° C., <25° C., 15° C., or <6° C. In a sixth example of the method, optionally including one or more or each of the first through fifth examples, the selected liquid feed includes a low volatility organic solvent and the maximum temperature is <80° C., <70° C., or <60° C. In a seventh example of the method, optionally including one or more or each of the first through sixth examples, spray drying at the minimum drying rate includes spray drying in a spray drying system configured as a reference spray drying system and spray drying at the reduced minimum drying rate includes spray drying in a spray drying system configured as an extended spray drying system.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method of spray drying using a vacuum spray drying system, comprising:

experimentally determining an outlet temperature to achieve a minimum drying rate at an atmospheric pressure based on a selected liquid feed and a selected liquid to gas ratio, wherein the selected liquid feed includes a liquid phase and a product;

calculating a predicted dryer pressure at which the minimum drying rate can be reached at a reduced outlet temperature with respect to a drying rate change relative to the minimum drying rate using a model based on a liquid feed drop which is pure liquid phase to approximate formation of a shell of the product on the liquid feed drop, wherein the reduced outlet temperature is less than a maximum temperature; and spray drying the selected liquid feed at the selected liquid to gas ratio, the predicted dryer pressure, and the reduced outlet temperature via the vacuum spray drying system, wherein the vacuum spray drying system includes a drying chamber to receive the selected liquid feed and a vacuum pump fluidly coupled to the drying chamber to reduce an operating pressure within the drying chamber and wherein the predicted dryer pressure is in a range between 0.01 bar up to 0.05 bar below ambient pressure.

2. The method of claim 1, wherein the product includes nucleic acids.

3. The method of claim 1, wherein the maximum temperature depends on the product included in the liquid phase.

4. The method of claim 1, wherein the reduced outlet temperature is less than a boiling point of the liquid phase at the predicted dryer pressure.

5. The method of claim 1, wherein the product is an active pharmaceutical ingredient.

6. The method of claim 1, wherein experimentally determining the reduced outlet temperature includes experimentation using a reference spray drying system to calculate the reduced outlet temperature for different drying chamber pressures.

7. The method of claim 1, wherein spray drying the selected liquid feed further includes controlling a jacket temperature of a jacketed drying chamber.

8. The method of claim 1, wherein a minimum dryer chamber pressure is decreased by a heat exchanger placed downstream of a cyclone and upstream of the vacuum pump.

9. The method of claim 1, wherein the selected liquid feed includes water and the maximum temperature is <35° C., <25° C., 15° C., or <6° C. or the selected liquid feed includes a low volatility organic solvent and the maximum temperature is <80° C., <70° C., or <60° C.

10. The method of claim 1, wherein spray drying at the minimum drying rate includes spray drying in a spray drying system configured as a reference spray drying system and spray drying at a reduced minimum drying rate includes spray drying in a spray drying system configured as an extended spray drying system.

11. The method of claim 1, wherein a minimum dryer chamber pressure is decreased by increasing a size of a cyclone positioned downstream of the drying chamber.

12. A method of spray drying using a vacuum spray drying system, comprising:

experimentally determining an outlet temperature to achieve a minimum drying rate at an atmospheric pressure based on a selected liquid feed and a selected liquid to gas ratio, wherein the selected liquid feed includes a liquid phase and a product;

calculating a predicted dryer pressure at which the minimum drying rate can be reached at a reduced outlet temperature with respect to a drying rate change relative to the minimum drying rate using a model based on a liquid feed drop which is pure liquid phase to approximate for formation of a shell of the product on the liquid feed drop, wherein the reduced outlet temperature is less than a maximum temperature; and spray drying the selected liquid feed at the selected liquid to gas ratio, the predicted dryer pressure, and the reduced outlet temperature, wherein the product is a pharmaceutically active protein via the vacuum spray drying system, and wherein the vacuum spray drying system includes a drying chamber to receive the selected liquid feed and a vacuum pump fluidly coupled to the drying chamber to reduce an operating pressure within the drying chamber.

13. The method of claim 12, wherein the maximum temperature is a temperature at which the pharmaceutically active protein degrades.

14. The method of claim 12, wherein the pharmaceutically active protein is an antibody.

* * * * *